US011123313B2

(12) United States Patent
Wellman et al.

(10) Patent No.: US 11,123,313 B2
(45) Date of Patent: Sep. 21, 2021

(54) METHODS AND COMPOSITIONS FOR TREATING SLEEP APNEA

(71) Applicant: The Brigham and Women's Hospital, Inc., Boston, MA (US)

(72) Inventors: D. Andrew Wellman, Wayland, MA (US); Luigi Taranto-Montemurro, Chestnut Hill, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 36 days.

(21) Appl. No.: 16/609,048

(22) PCT Filed: Apr. 26, 2018

(86) PCT No.: PCT/US2018/029518
§ 371 (c)(1),
(2) Date: Oct. 28, 2019

(87) PCT Pub. No.: WO2018/200775
PCT Pub. Date: Nov. 1, 2018

(65) Prior Publication Data
US 2020/0054583 A1    Feb. 20, 2020

Related U.S. Application Data

(60) Provisional application No. 62/558,814, filed on Sep. 14, 2017, provisional application No. 62/491,504, filed on Apr. 28, 2017.

(51) Int. Cl.
*A61K 31/137* (2006.01)
*A61P 1/00* (2006.01)
*A61K 9/00* (2006.01)
*A61K 31/216* (2006.01)

(52) U.S. Cl.
CPC .......... *A61K 31/137* (2013.01); *A61K 9/0053* (2013.01); *A61K 31/216* (2013.01); *A61P 1/00* (2018.01)

(58) Field of Classification Search
CPC .................................. A61K 31/137
See application file for complete search history.

(56) References Cited

U.S. PATENT DOCUMENTS

| 6,294,582 B1 | 9/2001 | Jerussi |
| 2002/0010216 A1 | 1/2002 | Rogosky et al. |
| 2006/0039867 A1 | 2/2006 | Rao et al. |

FOREIGN PATENT DOCUMENTS

| WO | WO 2006/069030 | 6/2006 |
| WO | WO 2019/152475 | 8/2019 |

OTHER PUBLICATIONS

Notice of Opposition in corresponding Colombian Appln. No. NC2019/0013180, dated Jun. 30, 2020, 13 pages (with English translation).
Barnes, "Muscarinic receptor subtypes in airways," Life Sciences, Jan. 1, 1993, 52(5-6):521-7.
clinicaltrials.gov, "Atomoxetine and Oxybutynin in Obstructive Sleep Apnea (ATOSA)," Sep. 21, 2016, retrieved on Oct. 26, 2020 from URL <https://clinicaltrials.gov/ct2/show/nct02908529?draw=2>, 7 pages.
DrugBank Accession No. DB00245, "Benzatropine," Jun. 13, 2005, 1 page.
DrugBank Accession No. DB00782, "Propantheline," Jun. 13, 2005, 1 page.
DiugBank Accession No. DB01062, "Oxybutynin" Jun. 13, 2005, 1 page.
DrugBank Accession No. DB08897, "Aclidinium," Jun. 4, 2013, 1 page.
DrugBank Accession No. DB09185, "Viloaxine," Oct. 16, 2015, 1 page.
fda.gov [online], "FDA approves first generic Strattera for the treatment of ADHD", May 30, 2017, retrieved Sep. 24, 2020 from URL <https://www.fda.gov/news-events/press-announcements/fda-approves-first-generic-strattera-treatment-adhd>, 1 page.
Matthews et al., "Selective noradrenaline reuptake inhibitors for schizophrenia," Cochrane Database of Systematic Reviews, Jan. 2018, (1), 129 pages.
EP Extended Search Report in European Appln. No. 18791670.5, dated Jan. 25, 2021, 12 pages.
GE Search Report in Georgian Appln. No. 15226/01, dated Dec. 21, 2020, 5 pages (with English summary).
Taranto-Montemurro et al., "The Combination of Atomoxetine and Oxybutynin Greatly Reduces Obstructive Sleep Apnea Severity," American Journal of Respiratory and Critical Care Medicine, May 2019, 199(10):1267-1276.
Berry et al., "Acute effects of paroxetine on genioglossus activity in obstructive sleep apnea," Sleep, Dec. 1999, 22(8):1087-1092.
Brooks et al., "Obstructive sleep apnea as a cause of systemic hypertension. Evidence from a canine model," J. Clin. Invest., Jan. 1997, 99(1):106-109.
Brownell et al., "Protriptyline in obstructive sleep apnea: a double-blind trial," N. Engl. J. Med., Oct. 1982, 307(17):1037-1042.
Chan et al., "Endogenous excitatory drive modulating respiratory muscle activity across sleep-wake states. American journal of respiratory and critical care medicine," Dec. 2006, 174(11):1264-1273.
ClinicalTrials.gov [online], "Atomoxetine and Oxybutynin in Obstructive Sleep Apnea (ATOSA)," Sep. 21, 2016, retrieved on Jun. 24, 2020, retrieved from URL<https://clinicaltrials.gov/ct2/show/NCT02908529?term=atomoxetine%2C+oxybutynin&cond=Sleep+Apnea&rank=1>, 7 pages.

(Continued)

*Primary Examiner* — Golam M Shameem
(74) *Attorney, Agent, or Firm* — Fish & Richardson P.C.

(57) ABSTRACT

Methods and compositions for the treatment of conditions associated with pharyngeal airway muscle collapse while the subject is in a non-fully conscious state, e.g., sleep apnea and snoring, comprising administration of a norepinephrine reuptake inhibitor (NRI) and a muscarinic receptor antagonist.

14 Claims, 11 Drawing Sheets

(56) References Cited

OTHER PUBLICATIONS

Eckert et al., "Defining phenotypic causes of obstructive sleep apnea. Identification of novel therapeutic targets," Am. J. Respir. Crit. Care. Med., Oct. 2013, 188(8):996-1004.
Eckert et al., "Eszopiclone Increases the Respiratory Arousal Threshold and Lowers the apnoea/hypopnoea Index in Obstructive Sleep Apnoea Patients With a Low Arousal Threshold," Clin. Sci. (Lond)., Jun. 2011, 120(12):505-514.
Edwards et al., "Acetazolamide improves loop gain but not the other physiological traits causing obstructive sleep apnoea," J. Physiol., Mar. 2012, 590(Pt 5):1199-1211.
Engleman et al., "Improving CPAP use by patients with the sleep apnoea/hypopnoea syndrome (SAHS)," Sleep Med. Rev., Feb. 2003, 7(1):81-99.
Fenik et al., "REM sleep-like atonia of hypoglossal (XII) motoneurons is caused by loss of noradrenergic and serotonergic inputs," Am. J. Respir. Crit. Care. Med., Nov. 2005, 172(10): 1322-1330.
Findley et al., "Automobile accidents involving patients with obstructive sleep apnea," Am. Rev. Respir. Dis., Aug. 1988, 138(2):337-340.
GE Office Action in Georgian Appln. No. 15226/01, dated May 19, 2020, 3 pages (with English language abstract).
Grace et al., "Identification of the mechanism mediating genioglossus muscle suppression in REM sleep," Am. J. Respir. Crit. Care. Med., Feb. 2013, 187(3):311-319.
Grace et al., "K+ channel modulation causes genioglossus inhibition in REM sleep and is a strategy for reactivation," Respir. Physiol. Neurobiol., Sep. 2013, 188(3):277-288.
Hanzel et al., "Response of Obstructive Sleep Apnea to Fluoxetine and Protriptyline," Chest, Aug. 1991, 100(2):416-21.
Hoffstein, "Blood pressure, snoring, obesity, and nocturnal hypoxaemia," Lancet, Sep. 1994, 344(8923):643-645.
Hung et al., "Association of sleep apnoea with myocardial infarction in men," Lancet, Aug. 1990, 336(8710):261-264.
Kraiczi et al., "Effect of serotonin uptake inhibition on breathing during sleep and daytime symptoms in obstructive sleep apnea," Sleep, Jan. 1999, 22(1):61-67.
Kribbs et al., "Objective measurement of patterns of nasal CPAP use by patients with obstructive sleep apnea," The American Review of Respiratory Disease, Apr. 1993, 147:887-895.
Kubin et al., "Control of Upper Airway Motoneurons During REM Sleep," Apr. 1998, News Physiol. Sci., 13(2):91-97.
Lai et., "Changes in monoamine release in the ventral horn and hypoglossal nucleus linked to pontine inhibition of muscle tone: An in vivo microdialysis study," J Neurosci., 21(8):7384-7391.
Marshall et al., "Two Randomized Placebo-Controlled Trials to Evaluate the Efficacy and Tolerability of Mirtazapine for the Treatment of Obstructive Sleep Apnea," Sleep, Jun. 2008, 31(6):824-831.
Nieto et al., "Association of sleep-disordered breathing, sleep apnea, and hypertension in a large community-based study," Sleep heart health study, JAMA, Apr. 2000, 283(14):1829-1836.
PCT International Preliminary Report on Patentability in International Appln. PCT/US2018/029518, dated Oct. 29, 2019, 10 pages.
Peppard et al., "Increased Prevalence of Sleep-Disordered Breathing in Adults," Am. J. Epidemiol., May 2013, 177(9):1006-1014.
Peppard et al., "Prospective study of the association between sleep-disordered breathing and hypertension," The New England Journal of Medicine, May 2000, 342(19):1378-1384.
Redline et al., "Neuropsychological function in mild sleep-disordered breathing," Sleep, Feb. 1997, 20(2):160-167.
Ruehland et al., "The new AASM criteria for scoring hypopneas: Impact on the apnea hypopnea index," Sleep, Feb. 2009, 32(2):150-157.
Sangal et al., "Atomoxetine Improves Sleepiness and Global Severity of Illness but Not the Respiratory Disturbance Index in Mild to Moderate Obstructive Sleep Apnea With Sleepiness," Sleep Med., Jul. 2008, 9(5):506-510.
Shahar et al., "Sleep-disordered breathing and cardiovascular disease: Cross-sectional results of the sleep heart health study," Am. J. Respir. Crit. Care Med., Jan. 2001, 163(1):19-25.
Somers et al., "Sympathetic neural mechanisms in obstructive sleep apnea," J. Clin. Invest., Oct. 1995, 96(4):1897-1904.
Sood et al., "Genioglossus muscle activity and serotonergic modulation of hypoglossal motor output in obese Zucker rats," J. Appl. Physiol., Jun. 2007, 102(6):2240-2250.
Sood et al "Inhibition of serotonergic medullary raphe obscurus neurons suppresses genioglossus and diaphragm activities in anesthetized but not conscious rats," J. Appl. Physiol., Jun. 2006, 100:1807-1821.
Sood et al., "Role of endogenous serotonin in modulating genioglossus muscle activity in awake and sleeping rats," American Journal of Respiratory and Critical Care Medicine, Nov. 2005, 172(10): 1338-1347.
Taranto-Montemurro et al., "Effects of Tiagabine on Slow Wave Sleep and Arousal Threshold in Patients With Obstructive Sleep Apnea," Sleep, Feb. 2017, 40(2):zsw047, 7 pages.
Weaver & Gurnstein., "Adherence to Continuous Positive Airway Pressure Therapy: The Challenge to Effective Treatment," Proc. Am. Thorac. Soc., Feb. 2008, 5(2):173-178.
Wellman et al., "A method for measuring and modeling the physiological traits causing obstructive sleep apnea," J. Appl. Physiol., Jun. 2011, 110(6):1627-1637.
Wellman et al., "A simplified method for determining phenotypic traits in patients with obstructive sleep apnea," J. Appl. Physiol., Apr. 2013, 114(7):911-922.
Wellman et al., "Effect of oxygen in obstructive sleep apnea: Role of loop gain," Respir. Physiol. Neurobiol., Jul. 2008, 162(2):144-151.
Wessendorf et al., "Sleep-disordered breathing among patients with first-ever stroke," J. Neurol., Jan. 2000, 247(1):41-47.
Younes, "Contributions of upper airway mechanics and control mechanisms to severity of obstructive apnea," Am. J. Respir. Crit. Care Med., Sep. 2003, 168(6):645-658.
Young et al., "Burden of Sleep Apnea: Rationale, Design, and Major Findings of the Wisconsin Sleep Cohort Study," WMJ, Aug. 2009, 108(5):246-249.
Young et al., "Epidemiology of obstructive sleep apnea: a population health perspective," Am. J. Respir. Crit. Care. Med., May 2002;, 165(9):1217-1239.
International Search Report and Written Opinion dated Aug. 21, 2018 in international application No. PCT/US2018/029518, 16 pgs.
Taranto-Montemurro et al., "Desipramine Increases Genioglossus Activity and Reduces Upper Airway Collapsibility during Non-REM Sleep in Healthy Subjects," American Journal of Respiratory and Critical Care Medicine 194(7): 878-885 (Oct. 2016).

METHODS AND COMPOSITIONS FOR TREATING SLEEP APNEA

CLAIM OF PRIORITY

This application is a § 371 National Stage Application of PCT/US2018/029518, filed Apr. 26, 2018, which claims the benefit of U.S. Patent Application Ser. Nos. 62/491,504, filed on Apr. 28, 2017, and 62/558,814, filed on Sep. 14, 2017. The entire contents of the foregoing are hereby incorporated by reference.

FEDERALLY SPONSORED RESEARCH OR DEVELOPMENT

This invention was made with Government support under Grant No. HL095491 awarded by the National Institutes of Health. The Government has certain rights in the invention.

TECHNICAL FIELD

The present invention is based, at least in part, on the discovery of methods and compositions for the treatment of conditions associated with pharyngeal airway collapse while the subject is in a non-fully conscious state, e.g., snoring and sleep apnea, comprising administration of a norepinephrine reuptake inhibitor (NRI) and a muscarinic receptor antagonist.

BACKGROUND

Obstructive Sleep Apnea (OSA) is a common disorders[1] caused by collapse of the pharyngeal airway during sleep. OSA can have serious health consequences.

SUMMARY

The present disclosure is based upon the surprising discovery that the administration of noradrenergic and anti-muscarinic drugs can increase pharyngeal muscle activity in sleeping humans and reduce snoring and sleep apnea severity, e.g., in OSA patients.

Thus, provided herein are methods for treating a subject having a condition associated with pharyngeal airway collapse while the subject is in a non-fully conscious state. The methods include administering to a subject in need thereof an effective amount of (i) a norepinephrine reuptake inhibitor (NRI) and (ii) a muscarinic receptor antagonist.

In some embodiments, the NRI is a norepinephrine selective reuptake inhibitor (NSRI), e.g., an NSRI selected from the group consisting of Amedalin, Atomoxetine, CP-39,332, Daledalin, Edivoxetine, Esreboxetine, Lortalamine, Nisoxetine, Reboxetine, Talopram, Talsupram, Tandamine, and Viloxazine.

In some embodiments, the NRI is a norepinephrine non-selective reuptake inhibitor (NNRI), e.g., an NNRI selected from the group consisting of Amitriptiline, Amoxapine, Bupropion, Ciclazindol, Desipramine, Desvenlafaxine, Dexmethilphenidate, Diethylpropion, Doxepin, Duloxetine, Imipramine, Levomilnacipran, Manifaxine, Maprotiline, Methylphenidate, Milnacipran, Nefazodone, Nortriptyline, Phendimetrazine, Phenmetrazine, Protryptyline, Radafaxine, Tapentadol, Teniloxazine, and Venlafaxine.

In some embodiments, the NRI is selected from the group consisting of Atomoxetine and Reboxetine.

In some embodiments, the NRI is Atomoxetine, and in specific embodiments, the dosage of Atomoxetine is 20-100 mg, e.g., 25-75 mg.

In some embodiments, the muscarinic receptor antagonist is an M2 receptor agonist, e.g., is selected from the group consisting of atropine, propantheline, bethanechol, solifenacin, darifenacin, tolterodine, fesoterodine, trospium, and oxybutynin.

In some embodiments, the muscarinic receptor antagonist is selected from the group consisting of Anisotropine, Benztropine, Biperiden, Clidinium, Cycrimine, Dicyclomine, Diphemanil, Diphenidol, Ethopropazine, Glycopyrrolate, Hexocyclium, Isopropamide, Mepenzolate, Methixene, Methscopolamine, Oxyphencyclimine, Oxyphenonium, Procyclidine, Scopolamine, Tridihexethyl and Trihexyphenidyl.

In some embodiments, the muscarinic receptor antagonist is in an immediate release formulation.

In some embodiments, the muscarinic receptor antagonist is in an extended release formulation.

In some embodiments, the muscarinic receptor antagonist is Oxybutynin, and in specific embodiments, the dosage of Oxybutynin is 2-15 mg.

In some embodiments, the Oxybutynin is in an immediate release formulation, e.g., with a dose of 2.5-10 mg.

In some embodiments, the Oxybutynin is in an extended release formulation, e.g., with a dose of 5-15 mg.

In some embodiments, the disease or disorder is Obstructive Sleep Apnea (e.g., AHI of ≥10 events per hour) or Simple Snoring.

In some embodiments, the non-fully conscious state is sleep.

In some embodiments, the NRI and the muscarinic receptor antagonist are administered in a single composition.

In some embodiments, the single composition is an oral administration form.

In some embodiments, the oral administration form is a syrup, pill, tablet, troche, or capsule.

In some embodiments, the single composition is a transdermal administration form, e.g., a patch.

Also provided herein are pharmaceutical compositions comprising (i) a norepinephrine reuptake inhibitor (NRI) (ii) a muscarinic receptor antagonist, and (iii) a pharmaceutically acceptable carrier.

In some embodiments, the NRI is a norepinephrine selective reuptake inhibitor (NSRI), e.g., selected from the group consisting of Amedalin, Atomoxetine, CP-39,332, Daledalin, Edivoxetine, Esreboxetine, Lortalamine, Nisoxetine, Reboxetine, Talopram, Talsupram, Tandamine, and Viloxazine. In some embodiments, the NRI is a norepinephrine non-selective reuptake inhibitor (NNRI) selected from the group consisting of Amitriptiline, Amoxapine, Bupropion, Ciclazindol, Desipramine, Desvenlafaxine, Dexmethilphenidate, Diethylpropion, Doxepin, Duloxetine, Imipramine, Levomilnacipran, Manifaxine, Maprotiline, Methylphenidate, Milnacipran, Nefazodone, Nortriptyline, Phendimetrazine, Phenmetrazine, Protryptyline, Radafaxine, Tapentadol (Nucynta), Teniloxazine (Lucelan, Metatone) and Venlafaxine.

In some embodiments, the NRI is selected from the group consisting of Atomoxetine and Reboxetine.

In some embodiments, the NRI is Atomoxetine, and in specific embodiments, the dosage of Atomoxetine is 20-100 mg.

In some embodiments, the muscarinic receptor antagonist is an M2 antagonist, e.g., selected from the group consisting of atropine, propantheline, bethanechol, solifenacin, darifenacin, tolterodine, fesoterodine, trospium, and oxybutynin.

In some embodiments, the muscarinic receptor antagonist component of the pharmaceutical composition is selected from the group consisting of Anisotropine, Benztropine, Biperiden, Clidinium, Cycrimine, Dicyclomine, Diphemanil, Diphenidol, Ethopropazine, Glycopyrrolate, Hexocyclium, Isopropamide, Mepenzolate, Methixene, Methscopolamine, Oxyphencyclimine, Oxyphenonium, Procyclidine, Scopolamine, Tridihexethyl and Trihexyphenidyl. In some embodiments, the muscarinic receptor antagonist is in an immediate release formulation. In some embodiments, the muscarinic receptor antagonist is in an extended release formulation.

In some embodiments, the muscarinic receptor antagonist is Oxybutynin. In some embodiments, the Oxybutynin is in an immediate release formulation, e.g., with a dose of 2.5-10 mg. In some embodiments, the Oxybutynin is in an extended release formulation, e.g., with a dose of 5-15 mg.

Also provided are the compositions described herein for use in treating a subject having a condition associated with pharyngeal airway collapse while the subject is in a non-fully conscious state. In some embodiments, the disease or disorder is sleep apnea or Simple Snoring. In some embodiments, the disease or disorder is Obstructive Sleep Apnea.

In some embodiments, the non-fully conscious state is sleep.

In some embodiments, the NRI and the muscarinic receptor antagonist are administered in a single composition.

In some embodiments, the single composition is an oral administration form.

In some embodiments, the oral administration form is a pill, tablet, troche, or capsule.

Also provided herein are a norepinephrine reuptake inhibitor (NRI) and a muscarinic receptor antagonist, for use in treating a subject having a condition associated with pharyngeal airway collapse while the subject is in a non-fully conscious state.

Further, provided herein are kits comprising a norepinephrine reuptake inhibitor (NRI) and a muscarinic receptor antagonist, e.g., for use in method described herein, e.g., for treating a subject having a condition associated with pharyngeal airway collapse while the subject is in a non-fully conscious state. The kit can comprise, e.g., separate pharmaceutical compositions of any of the individual active drugs claimed herein with a pharmaceutically acceptable salt or carrier wherein said kit may contain (a) separate or common bottles or packets allowing potentially separate dosaging and (b) optionally a set of kit instructions.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
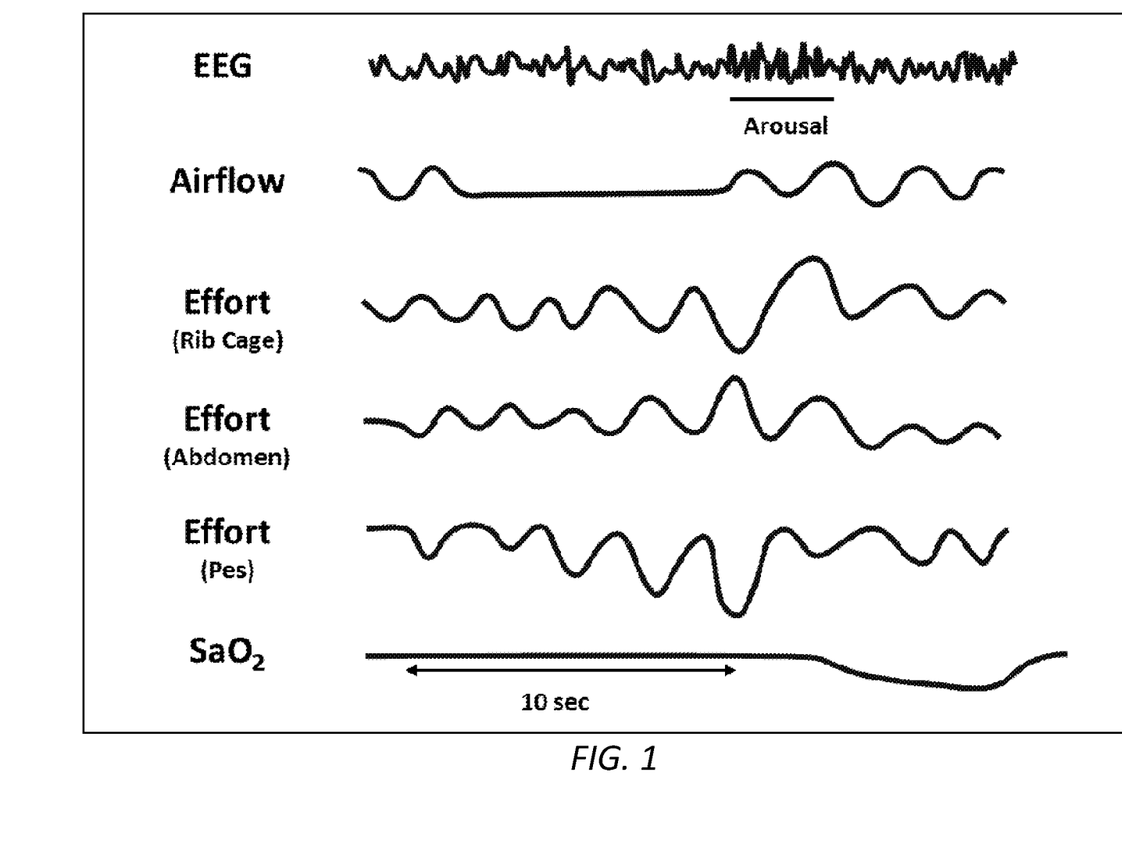
FIG. 1. Graphic illustration of an obstructive apnea. The top channel shows the electroencephalogram (EEG) pattern of sleep. The next channel represents airflow. The next three channels show ventilatory effort by movements of the rib cage and abdomen and changes in esophageal pressure, all of which reflect contraction of respiratory muscles. The last channel indicates oxyhemoglobin saturation.

In humans, the pharyngeal airway region has no bone or cartilage support, and it is held open by muscles. When these muscles relax during sleep, the pharynx can collapse resulting in cessation of airflow. As shown in FIG. 1, ventilatory effort continues and increases in an attempt to overcome the obstruction, shown by an increase in esophageal pressure change. Rib cage and abdominal movements are in the opposite direction as a result of the diaphragm contracting against an occluded airway, forcing the abdominal wall to distend out and the chest wall to cave inward.

Increasing efforts to breathe lead to an arousal from sleep, visualisable on an EEG (FIG. 1), and result in opening of the airway and a resumption of normal breathing. The lack of airflow during the apnea also causes hypoxia, shown by a drop in oxyhemoglobin saturation (FIG. 1). Severity is generally measured using the apnea-hypopnea index (AHI), which is the combined average number of apneas (cessation of breathing for at least ten seconds) and hypopneas (reduced airflow and oxygen saturation) that occur per hour of sleep. See, for example, Ruehland et al., The new AASM criteria for scoring hypopneas: Impact on the apnea hypopnea index. SLEEP 2009; 32(2): 150-157.

When a stringent definition of OSA is used (an AHI of ≥15 events per hour or AHI>5 events per hour with daytime sleepiness), the estimated prevalence is approximately 15 percent in males and 5 percent in females. An estimated 30 million individuals in the United States have OSA, of which approximately 6 million have been diagnosed. The prevalence of OSA in the United States appears to be increasing due to aging and increasing rates of obesity. OSA is associated with major comorbidities and economic costs, including: hypertension, diabetes, cardiovascular disease, motor vehicle accidents, workplace accidents, and fatigue/lost productivity. See, for example, Young et al., WMJ 2009; 108:246; Peppard et al., Am J Epidemiol 2013; 177:1006.

The present leading treatment[2,3] is continuous positive airway pressure (CPAP). CPAP is effective in virtually all patients, and approximately 85% of diagnosed patients are treated, but compliance is low. Patients find CPAP uncomfortable and often intolerable; at least 30% of patients (up to 80%) are regularly non-adherent and thus untreated (Weaver, Proc Am Thorac Soc. 2008 Feb. 15; 5(2): 173-178). Other treatment modalities with variable rates of success include oral appliances (10%) and surgery (5%), but neither is likely to be effective across the general population. No pharmacologic treatments have been shown to be effective to date.

The search for medicines to activate pharyngeal muscles in sleeping humans has been discouraging; agents such as serotonin reuptake inhibitors, tricyclic antidepressants, and sedatives have all been tested in humans and shown to be ineffective at reducing OSA severity. See, e.g., Proia and Hudgel, Chest. 1991 August; 100(2):416-21; Brownell et al., N Engl J Med 1982, 307:1037-1042; Sangal et al., Sleep Med. 2008 July; 9(5):506-10. Epub 2007 Sep. 27; Marshall et al., Sleep. 2008 June; 31(6):824-31; Eckert et al., Clin Sci (Lond). 2011 June; 120(12):505-14; Taranto-Montemurro et al., Sleep. 2017 Feb. 1; 40(2).

Surprisingly, we have discovered that the administration of noradrenergic and antimuscarinic drugs can increase pharyngeal muscle activity in sleeping humans and reduce snoring and sleep apnea severity in OSA patients.

Methods of Treatment

The methods described herein include methods for the treatment of disorders associated with pharyngeal airway muscle collapse during sleep. In some embodiments, the disorder is Obstructive Sleep Apnea (OSA) (defined as an AHI of ≥10 events per hour) or Simple Snoring. Generally, the methods include administering a therapeutically effective amount of a norepinephrine reuptake inhibitor and an antimuscarinic agent as known in the art and/or described herein, to a subject who is in need of, or who has been determined to be in need of, such treatment.

As used in this context, to "treat" means to ameliorate at least one symptom of the disorder associated with pharyngeal airway collapse. Often, pharyngeal airway collapse during sleep results in snoring and/or an interruption in breathing (apnea or hypopnea), arousal from sleep, and reduced oxygenation (hypoxemia); thus, a treatment can result in a reduction in one or more of snoring, apneas/hypopneas, sleep fragmentation, and hypoxemia.

Unexpectedly, administration of a therapeutically effective amount of a norepinephrine reuptake inhibitor and an antimuscarinic agent for the treatment of a subject having a condition associated with pharyngeal airway collapse while the subject is in a non-fully conscious state, such as OSA, will result in decreased AHI. In some embodiments, the administration of a therapeutically effective amount of a norepinephrine reuptake inhibitor and an antimuscarinic agent for the treatment of a subject having a condition associated with pharyngeal airway collapse while the subject is in a non-fully conscious state, such as OSA, will result in decreased AHI by 50% or more. In some embodiments, the administration of a therapeutically effective amount of a norepinephrine reuptake inhibitor and an antimuscarinic agent for the treatment of a subject having a condition associated with pharyngeal airway collapse while the subject is in a non-fully conscious state, such as OSA, will result in decreased AHI by 75% or more. In other further embodiments, the administration of a therapeutically effective amount of a norepinephrine reuptake inhibitor and an antimuscarinic agent for the treatment of a subject having a condition associated with pharyngeal airway collapse while the subject is in a non-fully conscious state, such as OSA, will result in increased ventilation. In yet other embodiments, the administration of a therapeutically effective amount of a norepinephrine reuptake inhibitor and an antimuscarinic agent for the treatment of a subject having a condition associated with pharyngeal airway collapse while the subject is in a non-fully conscious state, such as OSA, will result in increased oxygen blood levels. In still another embodiment, the administration of a therapeutically effective amount of a norepinephrine reuptake inhibitor and an antimuscarinic agent for the treatment of a subject having a condition associated with pharyngeal airway collapse while the subject is in a non-fully conscious state, such as OSA, will result in improved total sleep time, reduced AHI, increased oxygenation, less sleep fragmentation, increased total sleep time, and/or improved subjective sleep quality.

An effective amount of a norepinephrine reuptake inhibitor and an antimuscarinic agent can be administered in one or more administrations, applications or dosages, simultaneously or separately. When administered simultaneously, a norepinephrine reuptake inhibitor and an antimuscarinic agent can be formulated as a single dosage form, e.g., a capsule, tablet or solution, containing both a norepinephrine reuptake inhibitor and an antimuscarinic agent, or as separate dosage forms, e.g., one a capsule, tablet or solution, containing a norepinephrine reuptake inhibitor and another capsule, tablet or solution containing an antimuscarinic agent. Each of the norepinephrine reuptake inhibitor and the antimuscarinic agents can be administered, simultaneously or separately from one or more times per day to one or more times per week; including once every other day. In some embodiments, the norepinephrine reuptake inhibitor and the antimuscarinic agent are administered daily. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds (i.e., NRI and muscarinic receptor antagonist, in a single composition or in separate compositions) can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50.

The data obtained from cell culture assays and animal studies can be used in formulating a range of dosages for use in humans. The dosage of such compounds lies preferably within a range of circulating concentrations that include the ED50 with little or no toxicity. The dosage may vary within this range depending upon the dosage form employed and the route of administration utilized. The therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In some embodiments, the methods include administering a dose of 20-100 mg Atomoxetine (or a dose equivalent thereof of another NRI) and a dose of 2-15 mg Oxybutynin (or a dose equivalent thereof of another muscarinic receptor antagonist). In some embodiments, the methods include administering 80 mg Atomoxetine/5 mg Oxybutynin; 75 mg Atomoxetine/5 mg Oxybutynin; 75 mg Atomoxetine/6 mg Oxybutynin; 50 mg Atomoxetine/4 mg Oxybutynin; or 25 mg Atomoxetine/3 mg Oxybutynin. In other embodiments, the methods include administering a dose of 20-100 mg Atomoxetine (or a dose equivalent thereof of another NRI) and a dose of 2-15 mg Oxybutynin (or a dose equivalent thereof of another muscarinic receptor antagonist) within an hour of sleep time. In some embodiments, the methods include administering 80 mg Atomoxetine/5 mg Oxybutynin; 75 mg Atomoxetine/5 mg Oxybutynin; 75 mg Atomoxetine/6 mg Oxybutynin; 50 mg Atomoxetine/4 mg Oxybutynin; or 25 mg Atomoxetine/3 mg Oxybutynin, 15-60, e.g., 20-45, 15-25, or 20-30 minutes before sleep time.

In further embodiments, the methods include administering Atomoxetine/Oxybutynin in a 12.5 to 1 ratio by weight. In other embodiments, the methods include administering Atomoxetine/Oxybutynin in a 12.5 to 1 ratio by weight at 15-60, e.g., 20-45, 15-25, or 20-30, minutes before sleep time.

Pharmaceutical Compositions and Methods of Administration

The methods described herein include the use of pharmaceutical compositions comprising a norepinephrine reuptake inhibitor and an antimuscarinic agent as active ingredients. The norepinephrine reuptake inhibitor and antimuscarinic agent can be administered in a single composition or in separate compositions. In some embodiments, the methods include administering a norepinephrine reuptake inhibitor and an antimuscarinic agent, and no other active ingredients, i.e., the norepinephrine reuptake inhibitor and the antimuscarinic agent are the sole active agents.

Exemplary norepinephrine reuptake inhibitors (NRIs) include the selective NRIs, e.g., Amedalin (UK-3540-1), Atomoxetine (Strattera), CP-39,332, Daledalin (UK-3557-15), Edivoxetine (LY-2216684), Esreboxetine, Lortalamine (LM-1404), Nisoxetine (LY-94,939), Reboxetine (Edronax, Vestra), Talopram (Lu 3-010), Talsupram (Lu 5-005), Tandamine (AY-23,946), Viloxazine (Vivalan); and the non-selective NRIs, e.g., Amitriptiline, Amoxapine, Bupropion, Ciclazindol, Desipramine, Desvenlafaxine, Dexmethilphenidate, Diethylpropion, Doxepin, Duloxetine, Imipramine, Levomilnacipran, Manifaxine (GW-320,659), Maprotiline, Methylphenidate, Milnacipran, Nefazodone, Nortriptyline, Phendimetrazine, Phenmetrazine, Protryptyline, Radafaxine (GW-353,162), Tapentadol (Nucynta), Teniloxazine (Lucelan, Metatone) and Venlafaxine.

Suitable, but non-limiting, examples of antimuscarinics include Atropine, Propantheline, Bethanechol, Solifenacin, Darifenacin, Tolterodine, Fesoterodine, Trospium, and Oxybutynin, which have activity on the M2 receptor. Other exemplary antimuscarinics include Anisotropine, Benztropine, Biperiden, Clidinium, Cycrimine, Dicyclomine, Diphemanil, Diphenidol, Ethopropazine, Glycopyrrolate, Hexocyclium, Isopropamide, Mepenzolate, Methixene, Methscopolamine, Oxyphencyclimine, Oxyphenonium, Procyclidine, Scopolamine, Tridihexethyl, and Trihexyphenidyl.

In some embodiments, the norepinephrine reuptake inhibitor is Atomoxetine. In some embodiments, the antimuscarinic agent is Oxybutynin (e.g., N-desethyloxybutynin).

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., hypnotics including zolpidem, eszopiclone, benzodiazepines, gabapentin, tiagabine, and xyrem.

Pharmaceutical compositions are typically formulated to be compatible with their intended route of administration. Examples of routes of administration include systemic oral or transdermal administration.

Methods of formulating suitable pharmaceutical compositions are known in the art, see, e.g., *Remington: The Science and Practice of Pharmacy,* 21st ed., 2005; and the books in the series *Drugs and the Pharmaceutical Sciences: a Series of Textbooks and Monographs* (Dekker, N.Y.). For example, oral compositions generally include an inert diluent or an edible carrier. For the purpose of oral therapeutic administration, the active compound(s) can be incorporated with excipients and used in the form of pills, tablets, troches, or capsules, e.g., gelatin capsules. Oral compositions can also be prepared using a fluid carrier. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration of one or both of the compounds as described herein (i.e., one or both of a norepinephrine reuptake inhibitor and a muscarinic receptor antagonist) can also be by transdermal means, e.g., using a patch, gel, lotion, or thin film, to be applied to the skin. For transdermal administration, penetrants appropriate to the permeation of the epidermal barrier can be used in the formulation. Such penetrants are generally known in the art. For example, for transdermal administration, the active compounds can be formulated into ointments, salves, gels, or creams as generally known in the art. The gel and/or lotion can be provided in individual sachets, or via a metered-dose pump that is applied daily; see, e.g., Cohn et al., Ther Adv Urol. 2016 April; 8(2): 83-90.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration or use in a method described herein.

EXAMPLES

The invention is further described in the following examples, which do not limit the scope of the invention described in the claims.

Example 1. Pilot Study

In 3 healthy human individuals, the effect of the selective noradrenergic reuptake inhibitor, Atomoxetine 80 mg, in combination with the antimuscarinic drug Oxybutynin 5 mg on genioglossus muscle activity was measured in a pilot study.

Figure 2A:
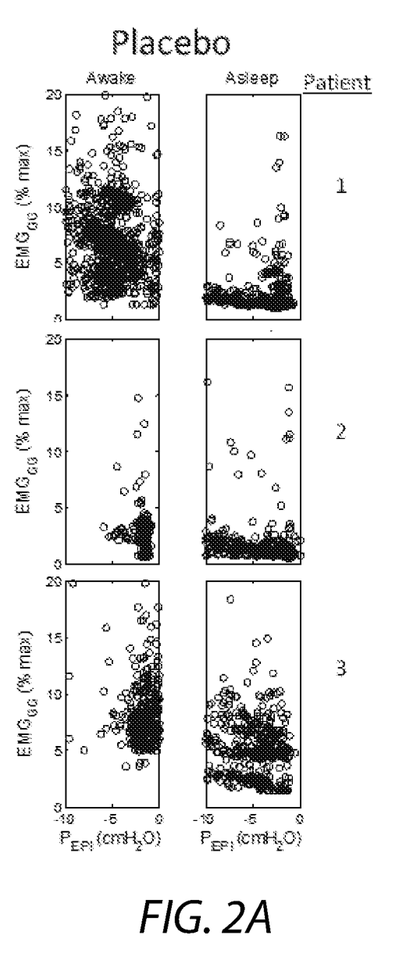
FIGS. 2A-2B. Pharyngeal muscle activity decreases from wake to sleep in the presence of a placebo (2A). In contrast, Atomoxetine+Oxybutynin preserves pharyngeal muscle activity near awake values during sleep (2B).
Figure 2B:
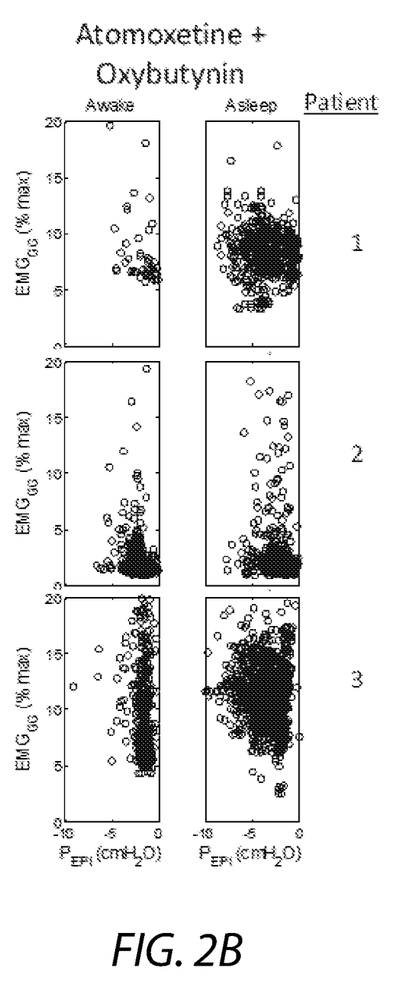

FIGS. 2A-B show data for the three individuals who took the combination of Atomoxetine and Oxybutynin. FIG. 2A is the placebo night. The graphs in the first column are the genioglossus muscle activity ($EMG_{GG}$, quantified as a percentage of maximum) during quiet wakefulness. Each circle represents the peak $EMG_{GG}$ of a single breath and is plotted against the corresponding epiglottic pressure. The graphs in the second column were obtained during stable NREM sleep. Note that there is a variable but clear reduction in $EMG_{GG}$ activity during sleep on the placebo night. In contrast, when these same three individuals took Atomoxetine+Oxybutynin, the sleep-related reduction in pharyngeal muscle activity was partially or completely prevented (FIG. 2B).

It is clear from this data that, compared to placebo, the tested drugs yielded a much higher $EMG_{GG}$ activity during NREM sleep. In the subjects exhibiting REM sleep on these drugs, $EMG_{GG}$ activity remained at 49% of the awake value in REM sleep, suggesting that the drugs are also effective in this stage as well.

Example 2. Crossover Study

Figure 3A:
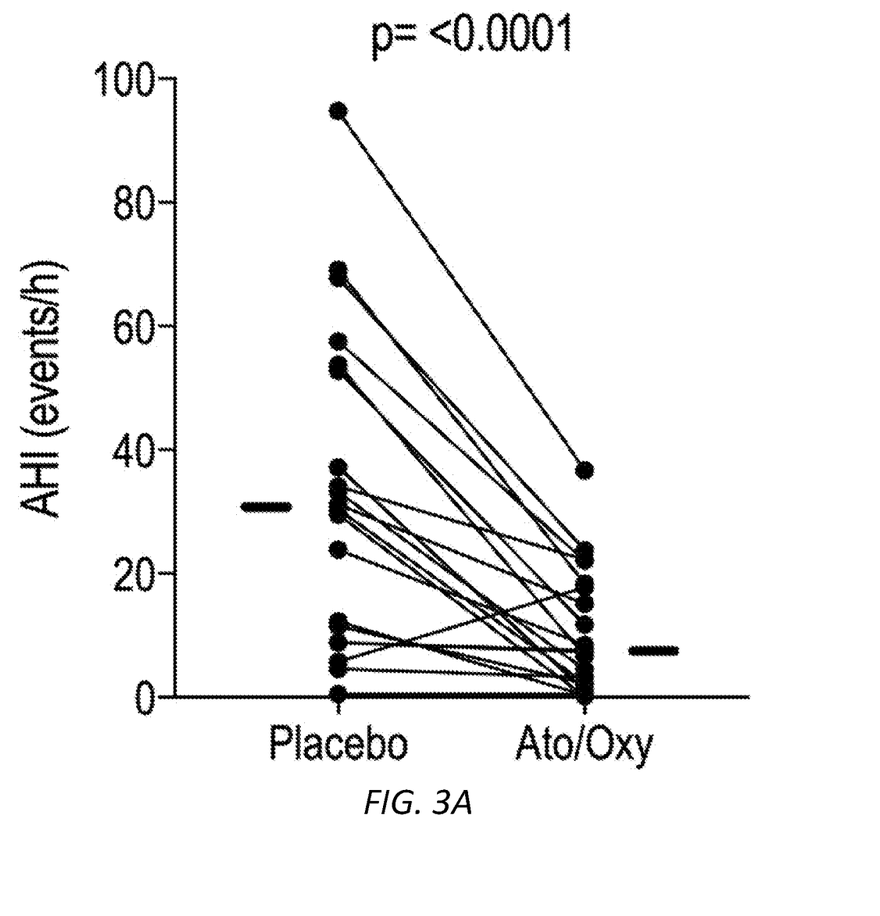
FIGS. 3A-3B. Participants received treatment (Atomoxetine 80 mg+Oxybutynin 5 mg) or placebo in randomized order 30 minutes before sleep. The results showed that the combination of Atomoxetine and Oxybutynin reduced the apnea hypopnea index (AHI) from 31 [10-54] to 8 [2-18] (3A). Data are expressed as median [25th-75th percentile]. When analysis of OSA severity was limited to the 15 subjects with an AHI>10 events hour, the effect of the combination of Atomoxetine/Oxybutynin was even greater (−78% of AHI compared to placebo) (3B).
Figure 3B:
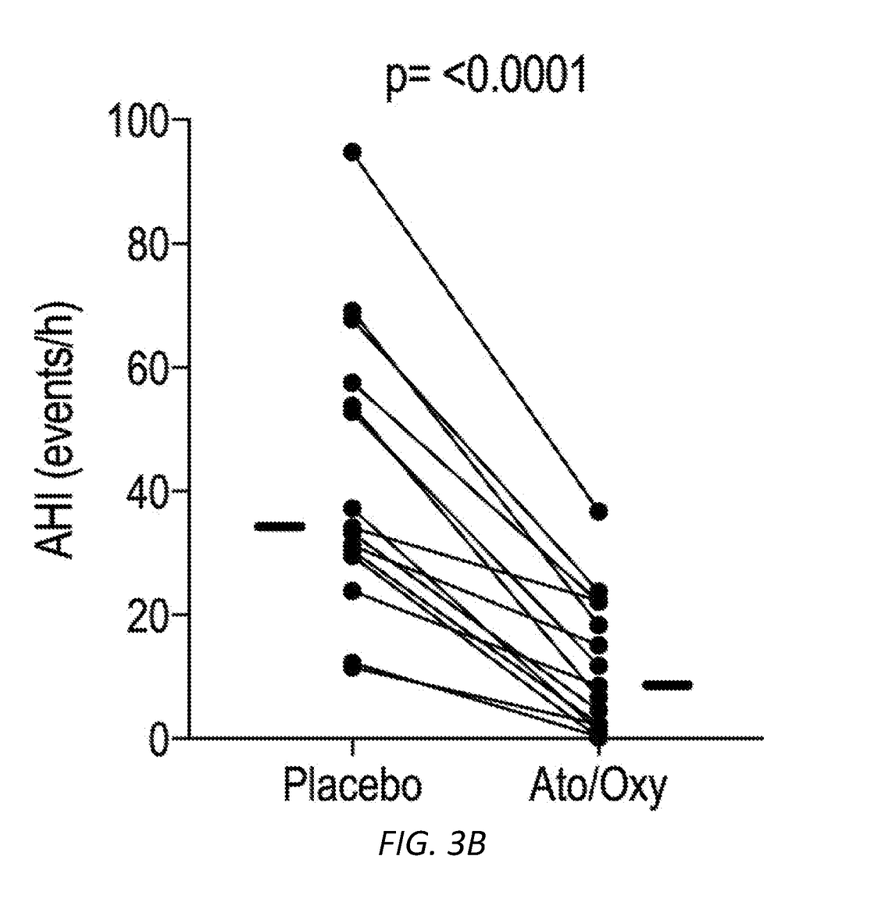

Subsequently, a placebo-controlled, double-blinded, randomized, crossover trial in 20 obstructive sleep apnea (OSA) human patients was performed. Participants received treatment (Atomoxetine 80 mg+Oxybutynin 5 mg) or placebo in randomized order 30 minutes before sleep. The trial showed that the combination of Atomoxetine and Oxybutynin reduced the apnea hypopnea index (AHI) from 31 [10-54] to 8 [2-18]. Data are expressed as median [25th-75th percentile] (FIG. 3A). During the trial, 5 subjects showed absence of clinically-significant OSA on the placebo night. If the analysis of OSA severity is limited to the 15 subjects with an AHI>10 events hour, the effect of the combination of Atomoxetine/Oxybutynin is even greater (78% reduction in AHI compared to placebo) (FIG. 3B). All OSA patients showed an improvement in OSA severity.

Figure 4:
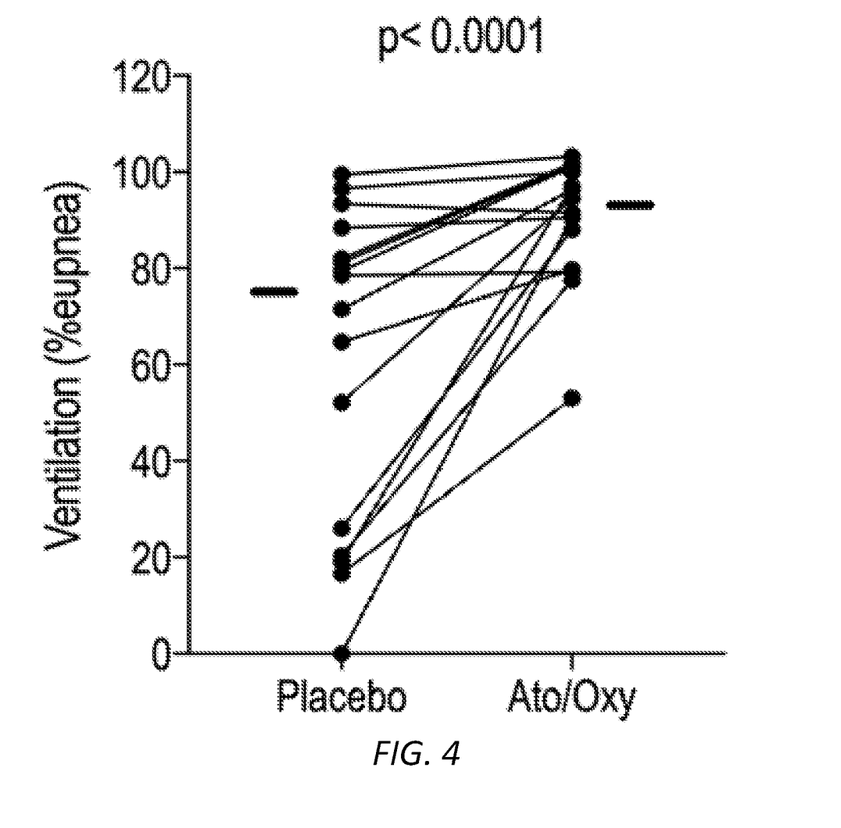
FIG. 4. The combination of Atomoxetine and Oxybutynin increased ventilation during sleep. Ventilation was calculated on placebo and drugs night as % of eupneic ventilation at normal ventilatory drive.

In these subjects, the combination of Atomoxetine and Oxybutynin increased the genioglossus muscle responsiveness to an increase in ventilatory drive compared to placebo from 0.1 to 0.3% max/$cmH_2O$, meaning that for each $cmH_2O$ increase in ventilatory drive (measured with esophageal pressure), the genioglossus muscle was activated 2 times more on the drugs compared to placebo. This improved upper airway muscle activity is likely the reason for the reduction in AHI (FIGS. 3A-B) and for the increased ventilation during sleep in these subjects (FIG. 4).

Figure 5:
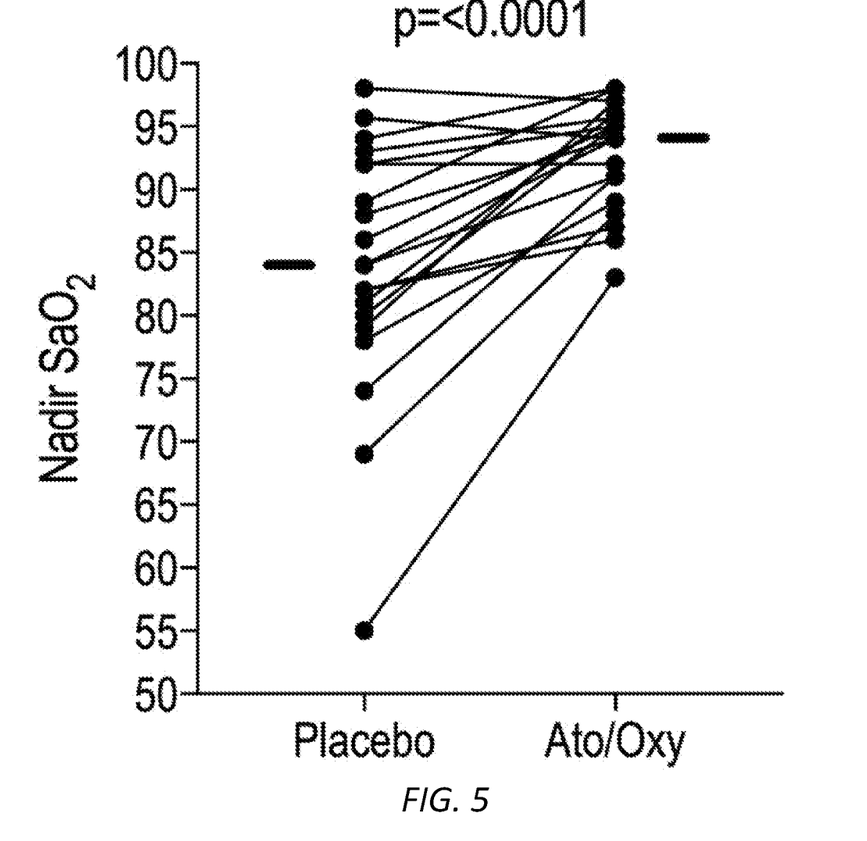
FIG. 5. OSA patients improved overnight lowest oxygen blood level from 84 [79-92] on placebo to 94 [89-95] during the Atomoxetine/Oxybutynin night.

Because of improved ventilation, oxygen levels (SaO2) were also increased on drugs night. The nadir of SaO2 went from 84% [79-92] on placebo to 94% [89-96] on drugs (FIG. 5), while the oxygen desaturation index (ODI) went from 13 [6-34] during placebo night to 3 [0-8] on the drugs.

Figure 6A:
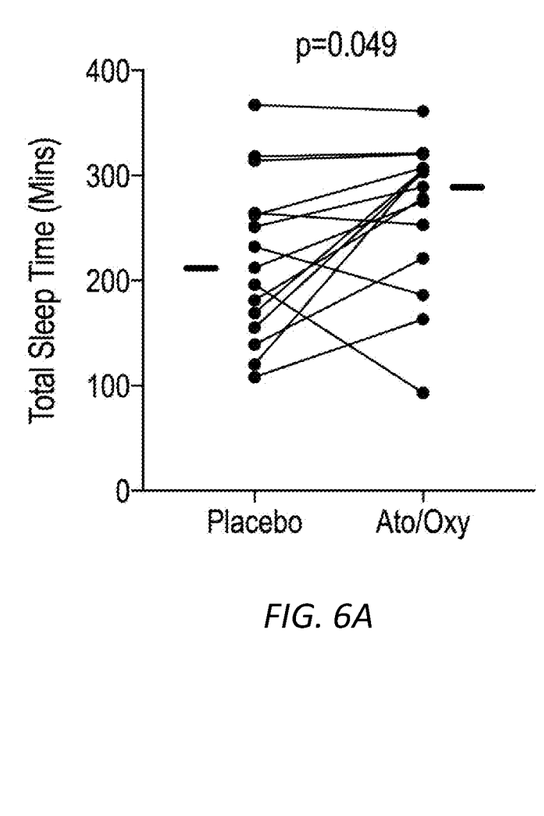
FIGS. 6A-6B. Total sleep time (6A) and sleep efficiency (6B) were also improved on Atomoxetine/Oxybutynin night compared to placebo for the subjects with an AHI>10.
Figure 6B:
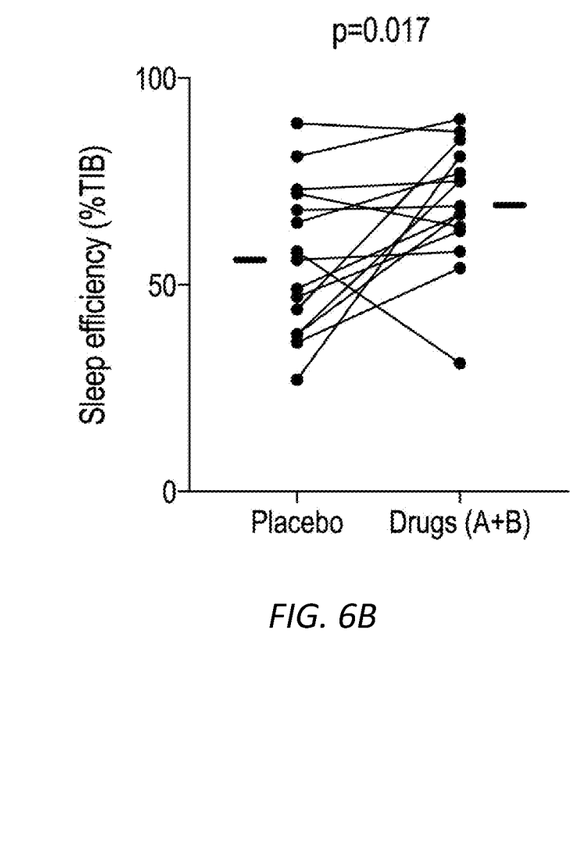

In addition, as shown in FIGS. 6A-B, total sleep time and sleep efficiency were also improved on the Atomoxetine/Oxybutynin night compared to placebo for the subjects with an AHI>10.

Figure 7:
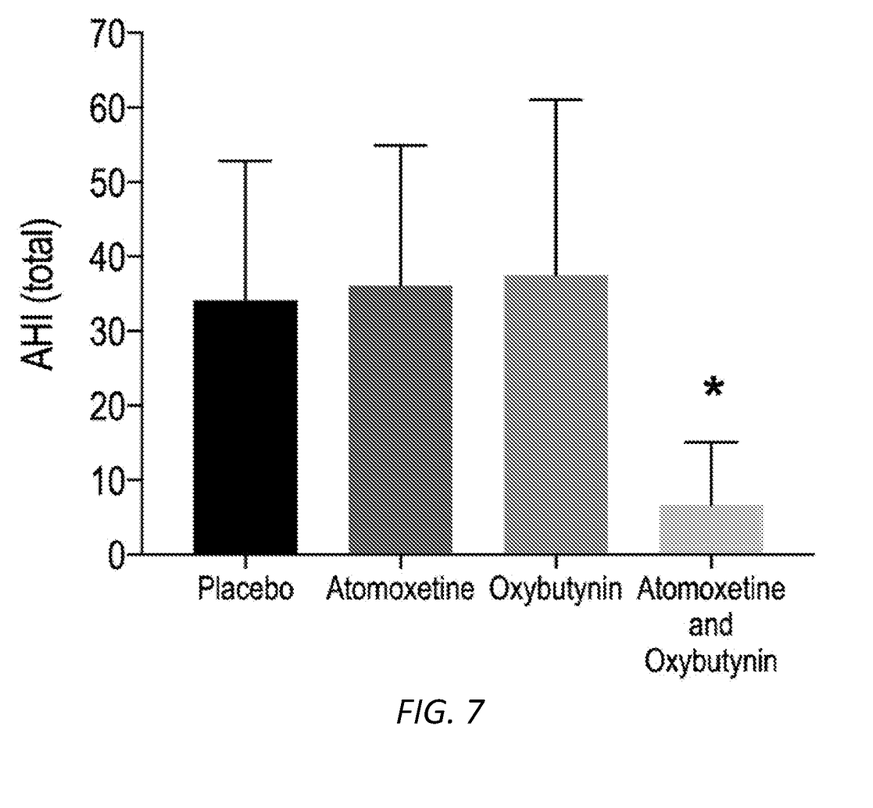
FIG. 7. Only the combination of Atomoxetine and Oxybutynin showed a significant reduction in AHI compared to placebo, while Atomoxetine or Oxybutynin alone did not improve the AHI.
Figure 8:
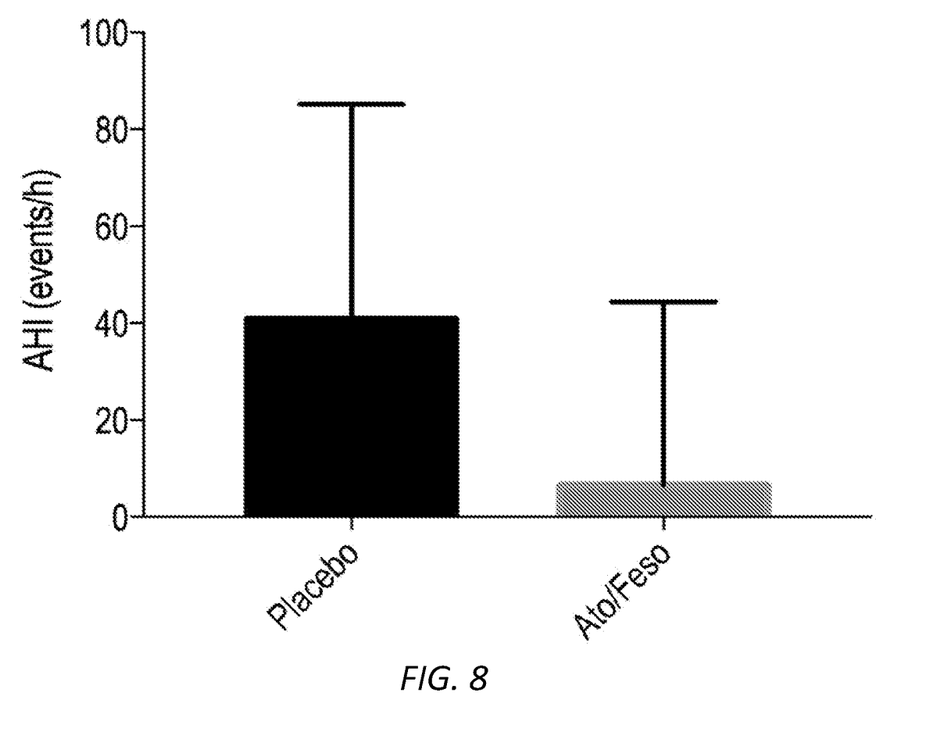
FIG. 8. In subjects with a mild to moderate upper airway collapsibility, Atomoxetine and Fesoterodine was as effective as Atomoxetine and Oxybutynin in reducing AHI.

Seven OSA patients were studied also on 2 additional nights in which the 2 drugs were administered alone (not in combination). As shown in FIG. 7, only the combination of Atomoxetine and Oxybutynin showed a significant reduction in AHI compared to placebo, while Atomoxetine or Oxybutynin alone did not improve the AHI.

Example 3. Fesoterodine Study

To determine whether other antimuscarinic agents could be used in place of Oxybutynin, 4 mg Fesoterodine (a newer, extended-release antimuscarinic drug) was used in combination with 80 mg Atomoxetine in 3 subjects with a mild to moderate upper airway collapsibility (ventilation during sleep with normal effort was above 50% of eupneic ventilation on placebo). In this subgroup of patients, Fesoterodine was as effective as Oxybutynin in reducing the AHI.

In two patients with severe upper airway collapsibility (ventilation during sleep was below 50% of normal ventilation), the combination of Atomoxetine/Fesoterodine did not reduce the AHI, whereas Atomoxetine/Oxybutynin did.

Example 4. Prospective Study

Figure 9:
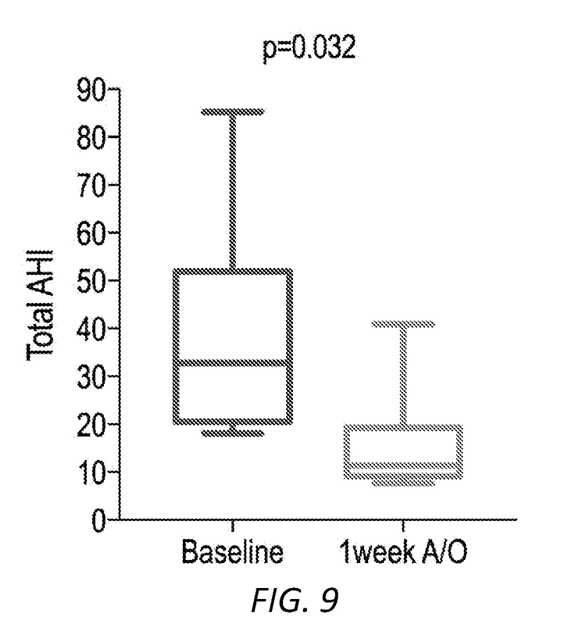
FIG. 9. In 6 subjects not treated with CPAP, administration of an Atomoxetine and Oxybutynin combination (Ato 80 mg/Oxy 5 mg) provided a 63% reduction in AHI after 1 week.

To evaluate the effect of the ato-oxy combination, a prospective study was performed over a week in 6 patients not treated with CPAP. The patients performed a baseline sleep study in hospital; drugs (Ato 80 mg/Oxy 5 mg) were administered for 6 nights at home, and on the 7th night the patients returned to the hospital to repeat the sleep study after taking the medications. These studies were performed with standard montage used for clinical sleep studies including electroencephalogram, electrooculogram, flow measurement with nasal cannula and thermistor, abdominal and thoracic belts, chin electromyography and oxygen saturation. The results, shown in FIG. 9, demonstrated a 63% [53 to 70] reduction in AHI after 1 week of therapy, suggesting that the drugs' effect is durable after a week of treatment.

In three patients we tested lower doses of the combination, i.e., Atomoxetine 80 mg in combination with Oxybutynin 5 mg, Atomoxetine 50 mg in combination with Oxybutynin 4 mg, and Atomoxetine 25 mg in combination with Oxybutynin 3 mg. The AHI showed a dose-dependent reduction compared to placebo, suggesting that lower doses than 80/5 mg may be effective in treating less severe disease. For the present purposes, we defined mild disease as 5<AHI<15, and moderate disease as 15<AHI<30 events/hour.

Figure 10A:
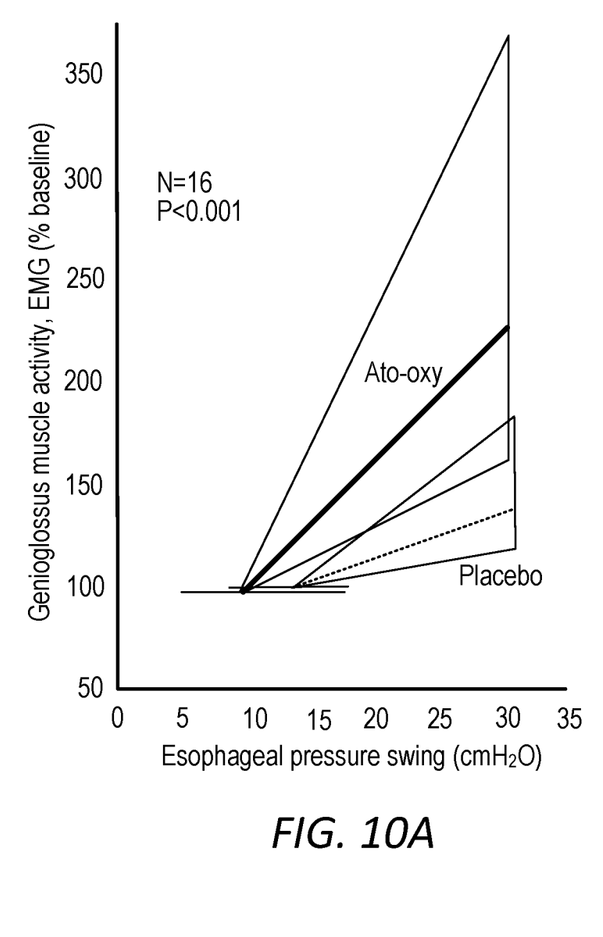
FIGS. 10A-10B. (10A) Group data showing the effect of Atomoxetine plus Oxybutynin (ato-oxy) on genioglossus muscle responsiveness. Shaded areas represent interquartile range of the slopes. Horizontal error bars illustrate interquartile range of baseline Pes; baseline values ($EMG_{GG}$=100%) are offset vertically to facilitate visualization of error bars. (10B) Example raw data are shown to provide context. Signals illustrate a spontaneous increase in genioglossus muscle activity with increasing Pes swings during sleep. $EMG_{GG}$: electromyography of genioglossus; mta: moving time average; Pes: esophageal pressure.
Figure 10B:
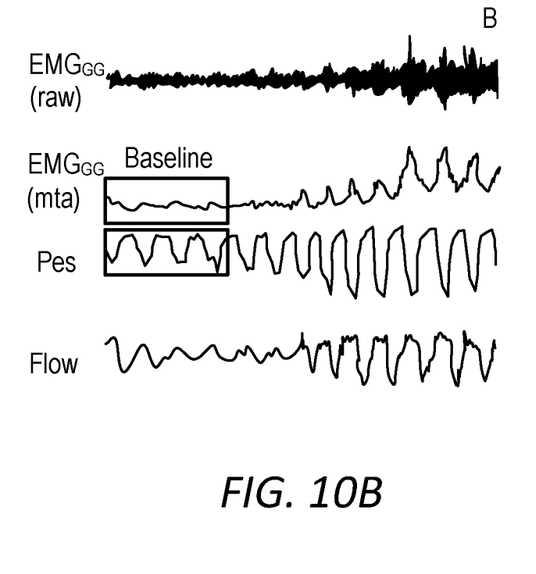

Group data was obtained using genioglossus electromyography in 16 out of 20 patients who took part to the original trial to determine the effect of Atomoxetine plus Oxybutynin (ato-oxy) on genioglossus muscle responsiveness. Muscle responsiveness reflects the change in genioglossus muscle electromyographic activity (percent of baseline) per change in esophageal pressure (Pes) swings during spontaneous breathing in non-REM sleep (see FIG. 10B for physiological context). Note that the median responsiveness on ato-oxy (slope of solid line) is greater than the responsiveness on placebo (slope of dashed line). FIG. 10B shows exemplary raw data to provide context. The signals illustrate a spontaneous increase in genioglossus muscle activity with increasing Pes swings during sleep. Note the restoration of airflow (Flow) accompanying increasing muscle activity.

REFERENCES

1. Young T, Peppard P E, Gottlieb D J. Epidemiology of obstructive sleep apnea: a population health perspective. Am J Respir Crit Care Med 2002; 165:1217-39.
2. Engleman H M, Wild M R. Improving CPAP use by patients with the sleep apnoea/hypopnoea syndrome (SAHS). Sleep Med Rev 2003; 7:81-99.
3. Kribbs N B, Pack A I, Kline L R, et al. Objective measurement of patterns of nasal CPAP use by patients with obstructive sleep apnea. The American review of respiratory disease 1993; 147:887-95.
4. Chan E, Steenland H W, Liu H, Homer R L. Endogenous excitatory drive modulating respiratory muscle activity across sleep-wake states. American journal of respiratory and critical care medicine 2006; 174:1264-73.
5. Grace K P, Hughes S W, Homer R L. Identification of the mechanism mediating genioglossus muscle suppression in REM sleep. Am J Respir Crit Care Med 2013; 187:311-9.
6. Kubin L, Davies R O, Pack A I. Control of Upper Airway Motoneurons During REM Sleep. News Physiol Sci 1998; 13:91-7.
7. Sood S, Morrison J L, Liu H, Homer R L. Role of endogenous serotonin in modulating genioglossus muscle activity in awake and sleeping rats. American journal of respiratory and critical care medicine 2005; 172:1338-47.
8. Sood S, Raddatz E, Liu X, Liu H, Homer R L. Inhibition of serotonergic medullary raphe *obscurus* neurons suppresses genioglossus and diaphragm activities in anesthetized but not conscious rats. J Appl Physiol (1985) 2006; 100:1807-21.
9. Fenik V B, Davies R O, Kubin L. REM sleep-like atonia of hypoglossal (XII) motoneurons is caused by loss of noradrenergic and serotonergic inputs. Am J Respir Crit Care Med 2005; 172:1322-30.
10. Sood S, Liu X, Liu H, Homer R L. Genioglossus muscle activity and serotonergic modulation of hypoglossal motor output in obese Zucker rats. J Appl Physiol (1985) 2007; 102:2240-50.
11. Hanzel D A, Proia N G, Hudgel D W. Response of obstructive sleep apnea to fluoxetine and protriptyline. Chest 1991; 100:416-21.
12. Kraiczi H, Hedner J, Dahlof P, Ejnell H, Carlson J. Effect of serotonin uptake inhibition on breathing during sleep and daytime symptoms in obstructive sleep apnea. Sleep 1999; 22:61-7.
13. Berry R B, Yamaura E M, Gill K, Reist C. Acute effects of paroxetine on genioglossus activity in obstructive sleep apnea. Sleep 1999; 22:1087-92.
14. Lai Y Y, Kodama T, Siegel J M. Changes in monoamine release in the ventral horn and hypoglossal nucleus linked to pontine inhibition of muscle tone: an in vivo microdialysis study. J Neurosci 2001; 21:7384-91.
15. Grace K P, Hughes S W, Shahabi S, Homer R L. K+ channel modulation causes genioglossus inhibition in REM sleep and is a strategy for reactivation. Respir Physiol Neurobiol 2013; 188:277-88.
16. Eckert D J, White D P, Jordan A S, Malhotra A, Wellman A. Defining phenotypic causes of obstructive sleep apnea. Identification of novel therapeutic targets. *Am J Respir Crit Care Med* 2013; 188:996-1004.
17. Wellman A, Eckert D J, Jordan A S, Edwards B A, Passaglia C L, Jackson A C, Gautam S, Owens R L, Malhotra A, White D P. A method for measuring and modeling the physiological traits causing obstructive sleep apnea. *J Appl Physiol* 2011; 110:1627-1637.
18. Wellman A, Edwards B A, Sands S A, Owens R L, Nemati S, Butler J P, Passaglia C L, Jackson A C, Malhotra A, White D P. A simplified method for determining phenotypic traits in patients with obstructive sleep apnea. *J Appl Physiol* 2013.
19. Younes M. Contributions of upper airway mechanics and control mechanisms to severity of obstructive apnea. *Am J Respir Crit Care Med* 2003; 168:645-658.
20. Somers V K, Dyken M E, Clary M P, Abboud F M. Sympathetic neural mechanisms in obstructive sleep apnea. *J Clin Invest* 1995; 96:1897-1904.
21. Nieto F J, Young T B, Lind B K, Shahar E, Samet J M, Redline S, D'Agostino R B, Newman A B, Lebowitz M D, Pickering T G. Association of sleep-disordered breathing, sleep apnea, and hypertension in a large community-based study. Sleep heart health study. *Jama* 2000; 283:1829-1836.
22. Brooks D, Homer R L, Kozar L F, Render-Teixeira C L, Phillipson E A. Obstructive sleep apnea as a cause of systemic hypertension. Evidence from a canine model. *J Clin Invest* 1997; 99:106-109.
23. Peppard P E, Young T, Palta M, Skatrud J. Prospective study of the association between sleep-disordered breathing and hypertension. *The New England journal of medicine* 2000; 342:1378-1384.
24. Hung J, Whitford E G, Parsons R W, Hillman D R. Association of sleep apnoea with myocardial infarction in men. *Lancet* 1990; 336:261-264.
25. Wessendorf T E, Teschler H, Wang Y M, Konietzko N, Thilmann A F. Sleep-disordered breathing among patients with first-ever stroke. *J Neurol* 2000; 247:41-47.
26. Hoffstein V. Blood pressure, snoring, obesity, and nocturnal hypoxaemia. *Lancet* 1994; 344:643-645.
27. Shahar E, Whitney C W, Redline S, Lee E T, Newman A B, Nieto F J, O'Connor G T, Boland L L, Schwartz J E, Samet J M. Sleep-disordered breathing and cardiovascular disease: Cross-sectional results of the sleep heart health study. *Am J Respir Crit Care Med* 2001; 163:19-25.

28. Redline S, Strauss M E, Adams N, Winters M, Roebuck T, Spry K, Rosenberg C, Adams K. Neuropsychological function in mild sleep-disordered breathing. *Sleep* 1997; 20:160-167.
29. Findley L J, Unverzagt M E, Suratt P M. Automobile accidents involving patients with obstructive sleep apnea. *Am Rev Respir Dis* 1988; 138:337-340.
30. Edwards B A, Sands S A, Eckert D J, White D P, Butler J P, Owens R L, Malhotra A, Wellman A. Acetazolamide improves loop gain but not the other physiological traits causing obstructive sleep apnoea. *J Physiol* 2012; 590: 1199-1211.
31. Wellman A, Malhotra A, Jordan A S, Stevenson K E, Gautam S, White D P. Effect of oxygen in obstructive sleep apnea: Role of loop gain. *Respir Physiol Neurobiol* 2008; 162: 144-151.
32. Lai Y Y, Kodama T, Siegel J M. Changes in monoamine release in the ventral horn and hypoglossal nucleus linked to pontine inhibition of muscle tone: An in vivo microdialysis study. *J Neurosci* 2001; 21:7384-7391.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject having a condition associated with pharyngeal airway collapse while the subject is in a non-fully conscious state, the method comprising administering to a subject in need thereof an effective amount of (i) a norepinephrine reuptake inhibitor (NRI) and (ii) a muscarinic receptor antagonist.

2. The method of claim 1, wherein the NRI is a norepinephrine selective reuptake inhibitor (NSRI) selected from the group consisting of Amedalin, Atomoxetine, CP-39,332, Daledalin, Edivoxetine, Esreboxetine, Lortalamine, Nisoxetine, Reboxetine, Talopram, Talsupram, Tandamine, and Viloxazine.

3. The method of claim 1, wherein the NRI is a norepinephrine non-selective reuptake inhibitor (NNRI) selected from the group consisting of Amitriptyline, Amoxapine, Bupropion, Ciclazindol, Desipramine, Desvenlafaxine, Dexmethylphenidate, Diethylpropion, Doxepin, Duloxetine, Imipramine, Levomilnacipran, Manifaxine, Maprotiline, Methylphenidate, Milnacipran, Nefazodone, Nortriptyline, Phendimetrazine, Phenmetrazine, Protriptyline, Radafaxine, Tapentadol, Teniloxazine, and Venlafaxine.

4. The method of claim 1, wherein the NRI is selected from the group consisting of Atomoxetine and Reboxetine.

5. The method of claim 1, wherein the NRI is Atomoxetine administered at a dose of 20-100 mg.

6. The method of claim 1, wherein the NRI is Atomoxetine, the muscarinic receptor antagonist is Oxybutynin, and the ratio of Atomoxetine to Oxybutynin is 12.5 to 1 by weight.

7. The method of claim 6, wherein the Atomoxetine is administered at a dose of 20 mg.

8. The method of claim 1, wherein the muscarinic receptor antagonist is selected from the group consisting of Atropine, Propantheline, Bethanechol, Solifenacin, Darifenacin, Tolterodine, Fesoterodine, Trospium, Oxybutynin, Anisotropine, Benztropine, Biperiden, Clidinium, Cycrimine, Dicyclomine, Diphemanil, Diphenidol, Ethopropazine, Glycopyrrolate, Hexocyclium, Isopropamide, Mepenzolate, Methixene, Methscopolamine, Oxyphencyclimine, Oxyphenonium, Procyclidine, Scopolamine, Tridihexethyl and Trihexyphenidyl.

9. The method of claim 1, wherein the muscarinic receptor antagonist is administered in an immediate release formulation or an extended release formulation.

10. The method of claim 1, wherein the muscarinic receptor antagonist is Oxybutynin administered at a dose of 2-15 mg.

11. The method of claim 1, wherein the disease or disorder is Obstructive Sleep Apnea or Simple Snoring.

12. The method of claim 1, wherein the non-fully conscious state is sleep.

13. The method of claim 1, wherein the NRI and the muscarinic receptor antagonist are administered in a single composition.

14. The method of claim 1, wherein the NRI is Atomoxetine and the muscarinic receptor antagonist is Oxybutynin.

* * * * *